US012533694B2

(12) United States Patent
Park et al.

(10) Patent No.: US 12,533,694 B2
(45) Date of Patent: Jan. 27, 2026

(54) SYSTEM FOR ATOMIZING AND EJECTING LIQUID FOR TRANSDERMAL DELIVERY

(71) Applicant: L'Oreal, Paris (FR)

(72) Inventors: Woo Ram Park, Kawasaki (JP); Shahid Naseer, Kawasaki (JP); Chin Kai Lee, Kawasaki (JP)

(73) Assignee: L'OREAL, Paris (FR)

( * ) Notice: Subject to any disclaimer, the term of this patent is extended or adjusted under 35 U.S.C. 154(b) by 282 days.

(21) Appl. No.: 18/268,414

(22) PCT Filed: Dec. 17, 2021

(86) PCT No.: PCT/JP2021/048070

§ 371 (c)(1),
(2) Date: Jun. 20, 2023

(87) PCT Pub. No.: WO2022/138883

PCT Pub. Date: Jun. 30, 2022

(65) Prior Publication Data

US 2024/0033757 A1 Feb. 1, 2024

(30) Foreign Application Priority Data

Dec. 23, 2020 (JP) ................................ 2020-213550
Jan. 20, 2021 (FR) ...................................... 2100527

(51) Int. Cl.
*B05B 7/24* (2006.01)
*A61M 11/06* (2006.01)

(52) U.S. Cl.
CPC ........... *B05B 7/2424* (2013.01); *A61M 11/06* (2013.01); *B05B 7/2478* (2013.01);
(Continued)

(58) Field of Classification Search
CPC ..... B05B 7/2424; B05B 7/2478; B05B 12/06; B05B 7/2418; A61M 11/06;
(Continued)

(56) References Cited

U.S. PATENT DOCUMENTS 4,033,511 A 7/1977 Chamberlin
8,753,117 B2 * 6/2014 Edwards ............... B05B 7/2418 601/162

(Continued)

FOREIGN PATENT DOCUMENTS

CN 1777479 A 5/2006
CN 102271611 A 12/2011

(Continued)

OTHER PUBLICATIONS

International Search Report for counterpart Application No. PCT/JP2021/048070, dated Apr. 14, 2022.

(Continued)

*Primary Examiner* — Qingzhang Zhou
(74) *Attorney, Agent, or Firm* — The Marbury Law Group PLLC

(57) ABSTRACT

The present invention relates to a system (10) for atomizing and ejecting a liquid (L) for a transdermal delivery. The system (10) comprises: a tank (100) for holding the liquid (L); a Venturi tube (200) comprising a longitudinal central axis ($X_1$) and an internal passage (210) extending along the axis ($X_1$), wherein the internal passage (210) is fluidly connected to the tank (100) via an orifice (220) defined in the Venturi tube (200), wherein the internal passage (210) comprises a converging section (230), a diverging section (240) and a throat section (250) located between the converging and diverging sections (230, 240); a cylinder (300) comprising a longitudinal central axis ($X_2$), an end wall
(Continued)

(310) orthogonal to the axis ($X_2$), a circumferential wall (320) extending from the end wall (310) along the axis ($X_2$) and an outlet hole (330) formed on the end wall (310), wherein the outlet hole (330) is fluidly connected to an inlet (232) of the converging section (230); a piston (400) arranged in the cylinder (300) so as to be displaceable in the cylinder (300) along the axis ($X_2$), wherein the piston (400) defines an air intake space (V) in the cylinder (300) in cooperation therewith, wherein the air intake space (V) fluidly communicates with the inlet (232) of the converging section (230) via the outlet hole (330); a driving unit (500) for displacing the piston (400) in a direction in which a volume of the air intake space (V) increases; and an elastic member (600) that is deformed according to the displacement of the piston (400) and stores an elastic energy therein while the piston (400) is being displaced in the direction in which the volume of the air intake space (V) increases. The driving unit (500) comprises an elastic energy release mechanism (M) that releases the elastic energy stored in the elastic member (600), thereby causing the piston (400) to rush in a direction in which the volume of the air intake space (V) decreases.

18 Claims, 8 Drawing Sheets

(52) U.S. Cl.
CPC ... *A61M 2205/07* (2013.01); *A61M 2205/103* (2013.01); *A61M 2205/8281* (2013.01)

(58) Field of Classification Search
CPC ........ A61M 2205/07; A61M 2205/103; A61M 2205/8281; A61M 11/00; A61M 2205/10; A61M 35/00; G01F 11/021; F04F 5/24; F04B 35/01; F04B 35/04
See application file for complete search history.

(56) References Cited

U.S. PATENT DOCUMENTS

| | | | |
|---|---|---|---|
| 2010/0167236 A1 | 7/2010 | Edwards et al. | |
| 2014/0248579 A1 | 9/2014 | Edwards et al. | |
| 2017/0007449 A1 | 1/2017 | Nielsen | |
| 2018/0099104 A1 | 4/2018 | Tang | |
| 2018/0235807 A1* | 8/2018 | Nielsen | A61M 11/007 |
| 2019/0076861 A1 | 3/2019 | Gunn | |

FOREIGN PATENT DOCUMENTS

| | | | |
|---|---|---|---|
| CN | 103889215 | A | 6/2014 |
| CN | 104379086 | A | 2/2015 |
| CN | 205434603 | U | 8/2016 |
| GB | 859114 | A | 1/1961 |
| JP | S63-100963 | A | 5/1988 |
| JP | H07-22635 | A | 1/1995 |
| JP | 2014000517 | A | 1/2014 |
| KR | 101606440 | B1 | 3/2016 |
| WO | 2016/178118 | A1 | 11/2016 |

OTHER PUBLICATIONS

French Search Report for counterpart Application No. FR2100527, dated Jan. 20, 2021.
English Translation of Office Action in KR1020237020474, mailed Mar. 19, 2025, 18 pages.
Translation of Notice of Reasons for Refusal for counterpart Application No. JP 2020-213550, dated Jul. 1, 2024.
The State Intellectual Property Office of People's Republic of China, "First Office Action," issued in related Chinese Patent Application No. 202180087048.9, mailed Aug. 7, 2025, including Machine Translation (17 pages).

* cited by examiner

SYSTEM FOR ATOMIZING AND EJECTING LIQUID FOR TRANSDERMAL DELIVERY

CROSS REFERENCE TO RELATED APPLICATIONS

This is a National Stage Application of PCT/JP2021/048070, filed internationally on Dec. 17, 2021, which claims priority to Japanese Application No. 2020-213550, filed on Dec. 23, 2020, and French Application No. 2100527, filed on Jan. 20, 2021, all of which are incorporated by reference herein in their entireties.

TECHNICAL FIELD

The present invention relates to a system for atomizing and ejecting a liquid, such as for example, water, oil, lotion or the like, for a transdermal delivery, in particular, a shallow transdermal delivery. The present invention also relates to an apparatus for a transdermal delivery of a liquid, which includes such a system. The present invention further relates to a method for atomizing and ejecting a liquid for a transdermal delivery.

BACKGROUND ART

A cosmetic liquid, such as a liquid lotion including a hyaluronic acid, is typically applied to specific parts of the user's body, such as a face, hands, and arms, via a shallow transdermal delivery (i.e., a shallow depth skin delivery). For more effective transdermal delivery of such a liquid, it is desirable to atomize the liquid into micrometer-order fine droplets and to eject or spray it onto the desired part of the user's body.

In prior art, several devices are known for atomizing and ejecting a cosmetic liquid. Most of these conventional devices use a high pressure gas (for example, a carbon dioxide gas) or a compressed air for atomization and ejection of a cosmetic liquid. The devices that use a high pressure gas require a replaceable gas cartridge. This gas cartridge method has a drawback that if the device is used frequently, the gas cartridge is exhausted quickly and thus a frequent replacement thereof is required. The devices that use a compressed air, on the other hand, require an external source of compressed air, i.e., an external air compressor or an external air pump. This makes the device large as a whole. Such devices are difficult to move and transport, and are not particularly suitable for easy handling. Therefore, there is a need for improvements on the devices for atomizing and ejecting a liquid.

Examples of prior art techniques that are at least to some extent related to the technique disclosed herein are as follows. JP1995022635 (MARUI) describes a motorized spring-piston-gear mechanism to generate compressed air. US20180099104A1 (Gold NanoTech Inc.) describes a device that atomizes a liquid by using an electromagnetic valve to control a discharge of an amount of a pressurized air. In this device, a pressurized air passes through a Venturi tube to atomize the liquid. However, JP1995022635 is only intended to generate compressed air for a model air gun or an air pistol purpose in order to discharge a solid pellet/projectile. On the other hand, the device disclosed in US20180099104A1 is only configured to operate with an externally supplied pressurized air.

DISCLOSURE OF THE INVENTION

In view of the above, an object of the present invention is to provide a novel system and method for atomizing and ejecting a liquid (especially, a liquid formula with a high molecular weight) for a transdermal delivery, as well as a novel apparatus for a transdermal delivery of a liquid, which includes such a system.

In particular, an object of the present invention is to provide a novel system and apparatus for atomizing and ejecting a liquid for a transdermal delivery, which do not require a replaceable, i.e., single-use/disposable power source such as a high-pressure gas cartridge, and can therefore atomize and eject the liquid as many times as the user wants. Furthermore, an object of the present invention is to provide a novel system and apparatus for atomizing and ejecting a liquid for a transdermal delivery, which do not require an external supply source such as an air compressor or an air pump, and are therefore compact as a whole (i.e., small in a physical footprint) and easy to move, transport and handle.

In order to achieve the above-stated objects, the present invention provides a system for atomizing and ejecting a liquid for a transdermal delivery (in particular, a shallow transdermal delivery) as described below. That is, the system according to the preset invention comprises: (i) a tank for holding the liquid; (ii) a Venturi tube comprising: a longitudinal central axis; and an internal passage extending along this longitudinal central axis, wherein the internal passage is fluidly connected to the tank via an orifice defined in the Venturi tube, wherein the internal passage comprises: a converging section; a diverging section; and a throat section located between the converging section and the diverging section; (iii) a cylinder comprising: a longitudinal central axis; an end wall orthogonal to this longitudinal central axis; a circumferential wall extending from the end wall along the same longitudinal central axis; and an outlet hole formed on the end wall, wherein the outlet hole is fluidly connected to an inlet of the converging section of the Venturi tube; (iv) a piston arranged in the cylinder so as to be displaceable in the cylinder along the longitudinal central axis thereof, wherein the piston defines an air intake space in the cylinder in cooperation with the cylinder, wherein the air intake space fluidly communicates with the inlet of the converging section of the Venturi tube via the outlet hole of the cylinder; (v) a driving unit for displacing the piston in a direction in which a volume of the air intake space in the cylinder increases; and (vi) an elastic member that is deformed according to the displacement of the piston and stores an elastic energy therein while the piston is being displaced in the direction in which the volume of the air intake space increases. In the present invention, the driving unit comprises an elastic energy release mechanism that releases the elastic energy stored in the elastic member, thereby causing the piston to rush in a direction in which the volume of the air intake space decreases.

The present invention also provides an apparatus for a transdermal (in particular, a shallow transdermal) delivery of an atomized liquid, the apparatus comprising: the system for atomizing and ejecting a liquid for a transdermal delivery as described above; and a casing that at least partially houses the system.

The present invention further provides a method for atomizing and ejecting a liquid for a transdermal (in particular, a shallow transdermal) delivery. The method comprises: (i) filling a tank with the liquid, wherein the tank is fluidly connected to an internal passage of a Venturi tube via an orifice defined in the Venturi tube, wherein the internal passage of the Venturi tube comprises: a converging section; a diverging section; and a throat section located between the converging section and the diverging section; (ii) displacing a piston in a cylinder in a direction in which a volume of an air intake space in the cylinder increases, wherein the air intake space is defined between the piston and an end wall of the cylinder, wherein an outlet hole formed on the end wall of the cylinder is fluidly connected to an inlet of the converging section of the Venturi tube; (iii) deforming, while the piston is being displaced in the direction in which the volume of the air intake space increases, an elastic member that is arranged so as to be deformed according to the displacement of the piston and stores an elastic energy therein; (iv) releasing the elastic energy stored in the elastic member, thereby causing the piston to rush in a direction in which the volume of the air intake space decreases; and (v) atomizing and ejecting to outside the liquid supplied from the tank into the internal passage of the Venturi tube, by air pushed out from the cylinder through the outlet hole of the end wall of the cylinder with a rush of the piston.

According to the present invention, the system includes a compressed air source mainly consisting of the cylinder, the piston, the elastic member, and the driving unit, as well as the Venturi tube in fluid communication with the fluid tank. In the present invention, the driving unit displaces the piston in the cylinder with deformation of the elastic member, and thereby a predetermined amount of air is taken into the cylinder. Subsequently, by instantly releasing the elastic energy stored in the elastic member, the piston is pushed back to its original position in the cylinder and compresses the air in the cylinder. As a result, the high-pressure air is blown out from the outlet hole of the cylinder at high speed and introduced into the internal passage of the Venturi tube. As the high-speed air passes through the Venturi tube, the pressure inside it drops, so a small amount of liquid in the tank is taken into the internal passage of the Venturi tube. A small amount of liquid thus taken into is atomized inside the Venturi tube by the action of the high-speed air and ejected out of the Venturi tube together with the air. According to the present invention, it is possible in this way to provide a jet of finely atomized liquid, i.e., a high velocity atomized liquid particle, suitable for a transdermal delivery, in particular a shallow transdermal delivery. As is well-known by those skilled in the art, a liquid with a high molecular weight does not effectively penetrate into a skin by a mere superficial application. According to the present invention, since the liquid is sufficiently finely crushed, even a liquid having a high molecular weight can be effectively penetrated into the skin. Here, a shallow transdermal delivery means a delivery up to the upper epidermis of the skin.

Furthermore, the system, the apparatus, and the method according to the present invention do not require a replaceable, i.e., single-use/disposable motive power source such as a high-pressure gas cartridge in order to atomize and eject a liquid for a transdermal delivery. Therefore, the system, the apparatus, and the method according to the present invention can atomize and eject the liquid over and over again. In addition to this, the system, the apparatus, and the method according to the present invention do not require any external source such as an air compressor or an air pump. That is, a high-speed air jet for atomizing and discharging a liquid can be created internally. Therefore, the system and the apparatus can be compact as a whole enough to be handheld, and it is easy to move, transport and handle.

According to one preferred aspect of the present invention, the piston may comprise: a longitudinal central axis; an end wall facing the end wall of the cylinder; and a circumferential wall extending from the end wall along the longitudinal central axis. In this aspect, a rack extending along the longitudinal central axis may be formed on an outer surface of the circumferential wall of the piston. Also, in this aspect, the driving unit may comprise a sector gear having teeth only in a certain angle range, which meshes with the rack of the piston and drives it linearly. Furthermore, in this aspect, the combination of the sector gear and the rack may form the elastic energy release mechanism. According to this aspect, the mechanism for releasing the elastic energy stored in the elastic member can be made particularly simple and robust. However, other mechanisms/means that operate mechanically, electrically, electromagnetically, or fluidly for releasing the elastic energy stored in the elastic member may be adopted as appropriate.

According to one preferred aspect of the present invention, in the case that the driving unit comprises a sector gear, the driving unit may further comprise: an electric power supply; and an electric motor that is electrically connected to the electric power supply and directly or indirectly drives the sector gear rotationally. According to this aspect, the driving unit is particularly easy to operate.

According to one preferred aspect of the present invention, in the case that the driving unit comprises an electric motor, the driving unit may further comprise: a pinion coupled to an output shaft of the electric motor; and one or more gears that transmit a rotational motion of the pinion to the sector gear to drive it rotationally. In particular, the one or more gears may comprise: a bevel gear that meshes with the pinion; and a spur gear that meshes with both the bevel gear and the sector gear. According to this aspect, the output shaft of the motor and a rotating shaft of the sector gear can be arranged so as to be orthogonal to each other, so that the system can be made as compact as possible. In addition to this, the usage of such a combination of gears helps to position the electric motor appropriately, depending on the desired overall shape of the apparatus including the system.

According to one preferred aspect of the present invention, in the case that the driving unit comprises a bevel gear and a spur gear, the driving unit may further comprise a latch that meshes with the spur gear, wherein the latch regulates a direction of rotation of the spur gear so that the spur gear rotates in only one direction. According to this aspect, the latch can prevent the reverse rotation of the spur gear and thus the backtracking of the piston due to the restoring force of the deformed elastic member. As a result, it is possible to prevent the piston from unintentionally operating to expel the air taken into the cylinder before the sector gear has been rotated to its final position where it disengages from the rack of the piston (i.e., before the elastic member stores a sufficient elastic energy).

According to one preferred aspect of the present invention, in the case that the driving unit comprises a sector gear, the circumferential wall of the cylinder may be formed with a linear notch for exposing at least a part of the rack of the piston, and the sector gear may mesh with the rack through the notch of the circumferential wall of the cylinder. According to this aspect, the system can be made more compact with respect to the displacement direction of the piston as compared to a case where the circumferential wall of the cylinder does not have a notch to expose at least part of the rack of the piston.

According to one preferred aspect of the present invention, in the case that the piston comprises the end wall facing the end wall of the cylinder and the circumferential wall extending from the end wall thereof, the elastic member may be a coil spring at least partially housed inside the piston. Also with this way, the system can be made compact with respect to the displacement direction of the piston. Furthermore, according to one preferred aspect of the present invention, the system may further comprise an elongated guide rod arranged so as to be surrounded by the elastic member, such as a coil spring. In this case, the guide rod may at least partially enter the piston when the piston is displaced in the direction in which the volume of the air intake space increases. According to this aspect, while making the system compact with respect to the displacement direction of the piston, it is possible for the elastic member, i.e., the coil spring to be reliably compressed as the piston is displaced.

According to one preferred aspect of the present invention, the tank may be fluidly connected to the throat section of the Venturi tube, in particular, via the orifice defined in the Venturi tube. According to this aspect, particularly efficient liquid atomization is possible. Also, according to one preferred aspect of the present invention, the Venturi tube may be directly connected to the cylinder such that the inlet of the converging section of the Venturi tube and the outlet hole of the cylinder are aligned with each other. According to this aspect, a particularly efficient ejection of an atomized liquid is possible as compared to a case where the inlet of the converging section of the Venturi tube and the outlet hole of the cylinder are connected, for example, by a separate pipeline or a separate conduit line.

According to one preferred aspect of the present invention, the ratio of the maximum inner diameter of the converging section of the Venturi tube, the inner diameter of the throat section of the Venturi tube, and the maximum inner diameter of the diverging section of the Venturi tube may be 1:0.1 to 0.7:1 to 1.5, based on the maximum inner diameter of the converging section. According to this aspect, a particularly satisfactory ejecting rate and ejecting amount of an atomized liquid can be achieved.

According to one preferred aspect of the present invention, the liquid may be a cosmetic liquid to be delivered transdermally, in particular, shallow-transdermally. However, according to the present invention, various liquids including a cosmetic liquid can be atomized and ejected. A suitable liquid for the present invention has, for example, a viscosity of $1\times10^{-4}$ Pa·s to 200 Pa·s, more preferably less than 70 Pa·s.

BRIEF DESCRIPTION OF THE DRAWINGS

Non-limiting and representative embodiments of the present invention will now be explained in detail below referring to the attached drawings.

DETAILED DESCRIPTION OF EMBODIMENTS

Some exemplary embodiments of the present invention will now be described with reference to FIGS. 1 to 8. In each figure, the scale ratio of width, length, height, diameter or the like of each element may not be constant, and may be different from the actual one. It should be noted that in certain figures, certain elements or features are drawn larger or smaller than they actually are, for emphasis.

As used herein, the terms related to the direction such as "upper", "lower", "up", "down", "upward", "downward", "above", "below", "right", "left" or the like should be understood in relation to the orientation of the system and the apparatus in the figures, which may or may not match the actual orientation in use. Furthermore, as is obvious to those skilled in the art, in this specification, the term "distal" or "distally" means a direction away from the Venturi tube that ejects or releases an atomized liquid. On the other hand, the term "proximal" or "proximally" means a direction closer to the Venturi tube.

Figure 1:
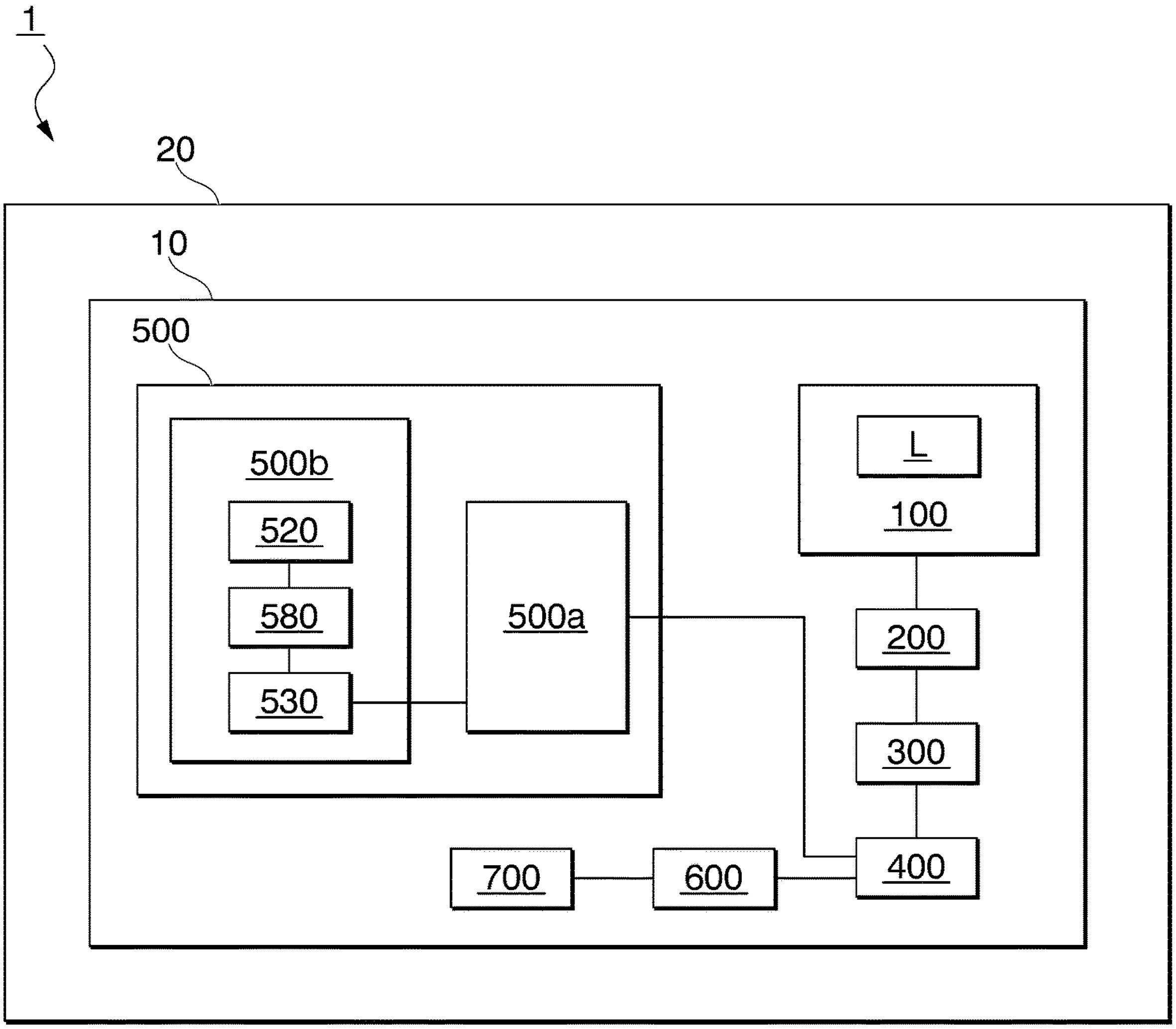
FIG. 1 is a schematic block diagram of an apparatus for a shallow transdermal delivery of atomized liquid according to one embodiment of the present invention.

FIG. 1 schematically shows an apparatus for a shallow transdermal delivery of an atomized liquid, which is an exemplary embodiment of the present invention. This apparatus, generally indicated by a reference numeral 1, mainly comprises a system, generally indicated by a reference numeral 10, for atomizing and ejecting a liquid for a transdermal delivery (explained in detail below), and a casing 20 that houses the system 10 therein. In the illustrated embodiment, the casing 20 approximately surrounds the entire system 10 (except for an outlet of a Venturi tube for discharging the atomized liquid), although the casing 20 may only house at least a portion of the system 10. The liquid that the apparatus 1 targets for atomization and ejection is, in particular, a cosmetic liquid such as a liquid lotion including a hyaluronic acid to be delivered transdermally. However, the apparatus 1 and thus the system 10 may be used for an atomization and an ejection of water, oil, various lotions, and the like.

Figure 2:
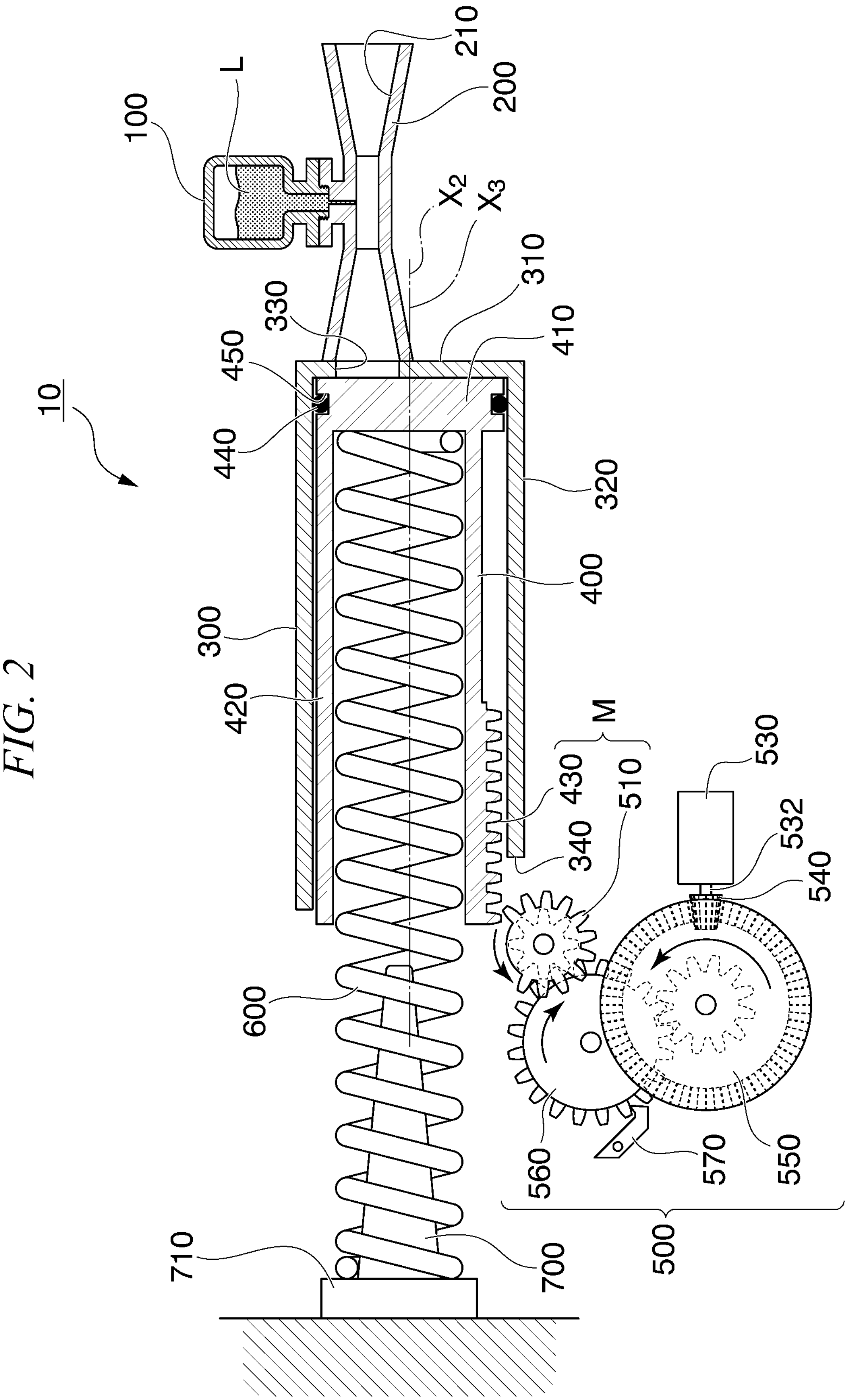
FIG. 2 is a schematic diagram of a system for atomizing and ejecting a liquid for a shallow transdermal delivery, which is to be incorporated into the apparatus shown in FIG. 1, wherein a Venturi tube, a piston and a cylinder that are components of the system are shown in cross section.

In addition to FIG. 1, as can be better seen from FIG. 2, the system 10 comprises a tank 100 for holding a certain amount of liquid L, for example a few milliliters to a few hundred milliliters of a liquid L. The tank 100 is preferably made of, for example, a transparent plastic or glass so that a content and/or an amount of the content can be seen from the outside. Translucent or opaque materials can be used for making the tank 100. The system 10 also comprises a Venturi tube 200, a cylinder 300 disposed adjacent to the Venturi tube 200, and a piston 400 slidably arranged in the cylinder 300. The Venturi tube 200 can be formed from a plastic material having a sufficient rigidity, for example, acrylonitrile butadiene styrene (ABS), polypropylene (PP), polycarbonate (PC) and the like. The cylinder 300 and the piston 400 can also be formed from the same material.

Instead, both the cylinder 300 and the piston 400 may be formed from the suitable metal (or metal alloy) material.

Further referring to FIGS. 1 and 2, the system 10 additionally comprises a driving unit 500 that is operatively (i.e., mechanically) associated with the piston 400, an elastic member 600 (a coil spring, in this embodiment) that is also mechanically associated with the piston 400, and an elongated guide rod 700 arranged so as to be surrounded by the coil spring 600.

Particularly, as shown in FIG. 1, the driving unit 500 mainly comprises a group of gears 500*a* and a power source assembly 500*b* described in detail below. In this embodiment, the power source assembly 500*b* includes a battery (electric power supply) 520, an electric motor 530, and a switch 580 interposed therebetween. It should be noted that the battery 520 and the switch 580 are not shown in figures other than FIG. 1 for convenience.

Figure 3:
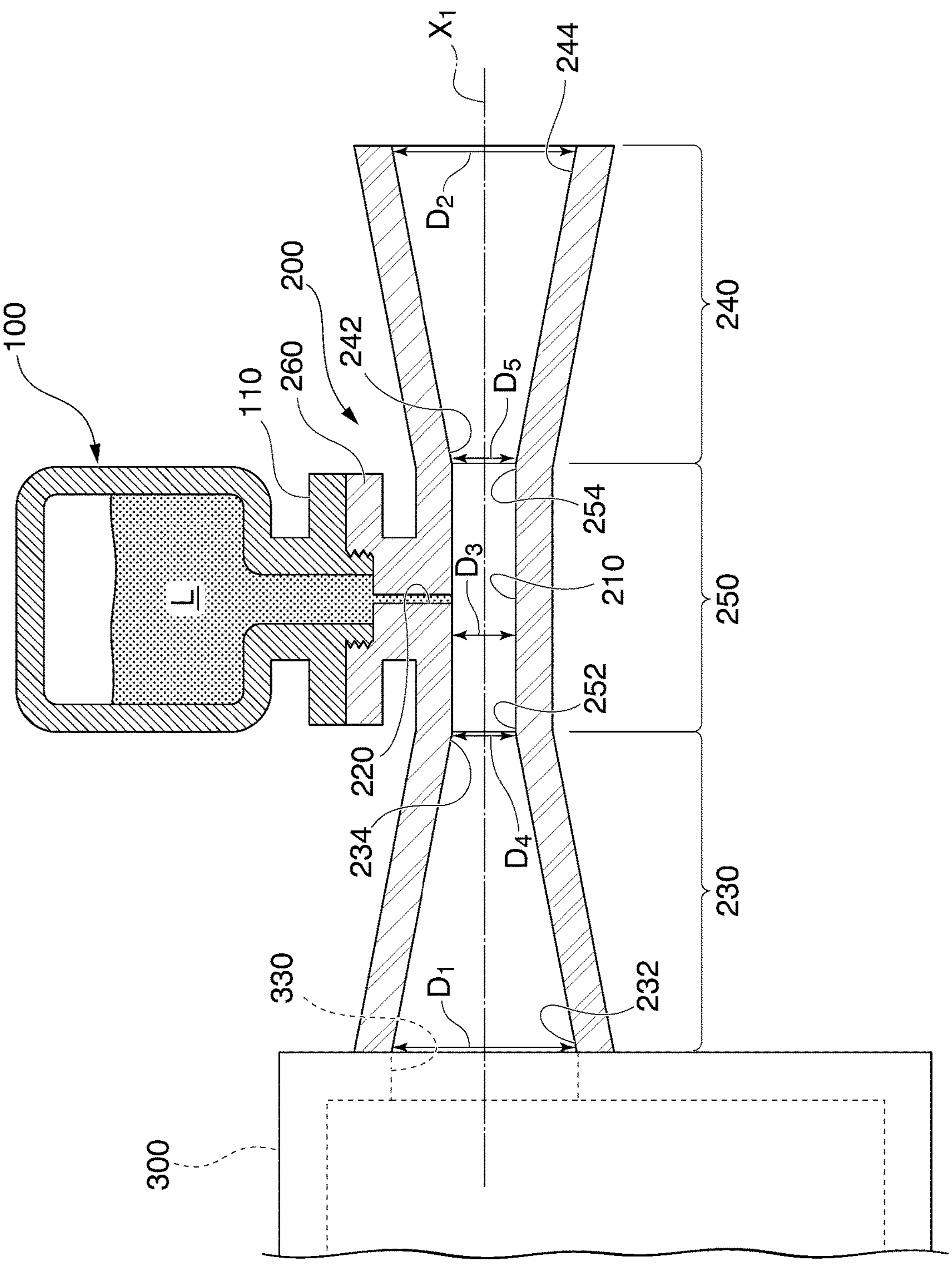
FIG. 3 is an enlarged cross-sectional view of the tank and the Venturi tube that are components of the system shown in FIG. 2.

As stated above and as shown in more detail in FIG. 3 which shows a cross-sectional view of the tank 100 and the Venturi tube 200, the system 10 comprises the tank 100 for holding the liquid L. In this embodiment, the tank 100 is detachably connected in a liquidtight manner to the Venturi tube 200 by way of screwing. The tank 100 has a flange 110 on the opening side thereof. The Venturi tube 200 also has a flange 260 corresponding to the flange 110 of the tank 100. The tank 100 is placed above the Venturi tube 200 with its flange 110 in contact with the flange 260 of the Venturi tube 200. This arrangement is particularly preferred as the action of gravity facilitates the supply of liquid L into the Venturi tube 200 during the system 10 operates. However, the orientation of the tank 100 with respect to the Venturi tube 200 is not limited to this exemplary embodiments and can be appropriately changed as needed.

Further referring to FIG. 3, the Venturi tube 200 comprises a longitudinal central axis $X_1$ and an internal passage 210 continuously extending along the longitudinal central axis $X_1$. The internal passage 210 is fluidly connected to the tank 100 via an orifice 220 defined in the Venturi tube 200. As shown in FIG. 3, the internal passage 210 comprises a converging section 230, a diverging section 240, and a throat section 250, which are connected continuously along the longitudinal central axis $X_1$. The throat section 250 is located between the converging section 230 and the diverging section 240. The tank 100 is fluidly connected, in particular, to the throat section 250 of the Venturi tube 200 via the orifice 220 as explained above. The inner diameter of the orifice 220 is such that when the pressure in the Venturi tube 200 is equal to the atmospheric pressure, the liquid L does not spontaneously drop in the Venturi tube 200 due to the viscosity of the liquid L.

The converging section 230 has an inlet 232 and an outlet 234 placed on each of two ends thereof. The throat section 250 also has an inlet 252 and an outlet 254 placed on each of two ends thereof. Furthermore, the diverging section 240 has an inlet 242 and an outlet 244 placed on each of two ends thereof. The outlet 234 of the converging section 230 and the inlet 252 of the throat section 250 connects with each other smoothly and continuously. Similarly, the outlet 254 of the throat section 250 and the inlet 242 of the diverging section 240 connects with each other smoothly and continuously.

In this embodiment, the inner diameter $D_3$ of the throat section 250 is constant. The inner diameter (minimum inner diameter) $D_4$ of the outlet 234 of the converging section 230 is the same as the inner diameter $D_3$ of the throat section 250, and the inner diameter (minimum inner diameter) $D_5$ of the inlet 242 of the diverging section 240 is also the same as the inner diameter $D_3$ of the throat section 250. The inner diameter of the converging section 230 decreases monotonically (linearly) towards the throat section 250, while the inner diameter of diverging section 240 increases monotonically (linearly) away from the throat section 250. However, the inner diameters of the converging and diverging sections 230, 240 may curvilinearly decrease and increase, respectively.

Also, in this embodiment, the ratio of the maximum inner diameter $D_1$ (i.e., the inner diameter of the inlet 232) of the converging section 230, the inner diameter $D_3$ of the throat section 250, and the maximum inner diameter $D_2$ (i.e., the inner diameter of outlet 244) of the diverging section 240, i.e, $D_1$:$D_3$:$D_2$, is 1:0.1 to 0.7:1 to 1.5. This is based on the maximum inner diameter $D_1$ of the converging section 230. However, this ratio is just an example, and various other ratios can be adopted as needed.

Here, turning to FIG. 2, the cylinder 300, which is one component of the system 1, comprises a longitudinal central axis $X_2$, an end (proximal end) wall 310 facing the Venturi tube 200 and orthogonal to the longitudinal central axis $X_2$, and a circumferential wall 320 extending from the end wall 310 along the longitudinal central axis $X_2$. That is, the cylinder 300 is a hollow body with one end open. Although not shown and not limited to this, the cylinder 300 is fixedly supported by a frame of the system 10 (for example, a subcase (not shown) of the apparatus 1). The cylinder 300 further comprises an outlet hole 330 formed on the end wall 310 thereof. The outlet hole 330 is fluidly connected to the inlet 232 of the converging section 230 of the Venturi tube 200. In this embodiment, the Venturi tube 200 is directly connected to the cylinder 300 such that the inlet 232 of the converging section 230 of the Venturi tube 200 and the outlet hole 330 of the cylinder 300 are aligned with each other. However, if necessary, it is also possible to adopt a configuration in which the inlet 232 of the converging section 230 and the outlet hole 330 of the cylinder 300 are connected via a pipeline or a conduit line.

In the cylinder 300, the piston 400, which is one component of the system 1, is arranged so as to be smoothly displaceable along the longitudinal central axis $X_2$ of the cylinder 300. The piston 400 comprises a longitudinal central axis $X_3$, an end (proximal end) wall 410 facing the end wall 310 of the cylinder 300, and a circumferential wall 420 extending from the end wall 410 along the longitudinal central axis $X_3$. Furthermore, the piston 400 comprises a rack 430 extending along the longitudinal central axis $X_3$. The rack 430 is integrally formed on an outer surface of the circumferential wall 420 of the piston 400, in particular, in approximately half the area on the distal end side of the circumferential wall 420. Although not shown in FIG. 2, the piston 400 defines an air intake space V in the cylinder 300 in cooperation with it (see FIGS. 5, 6, and 7). The air intake space V fluidly communicates with the inlet 232 of the converging section 230 of the Venturi tube 200 via the outlet hole 330 of the cylinder 300.

The piston 400 further comprises an O-ring (packing) 440 made of, for example, an elastomeric material. The O-ring 440 is fitted in a circular groove 450 formed in the end wall 410 of the piston 400. The O-ring 440 serves to maintain airtightness between the piston 400 and the inner surface of the cylinder 300. In this embodiment, the cross section of the piston 400 is a perfect circle in its end wall section where the O-ring 440 is located. However, in the circumferential wall section, the cross section of the piston 400 is a partial circle in which a part of the circle is cut off along a straight line parallel to its diameter. This is to secure a flat surface on the outer peripheral surface of the piston for arranging the rack

430 as described above. Of course, in another embodiment, other shapes may be adopted as the cross section of the circumferential wall section of the piston 400. Although not shown, in this embodiment, the system 10 further includes a mechanism or feature for preventing the piston 400 from rotating with respect to the cylinder 300.

In the state shown in FIG. 2, that is, the state in which the end wall 310 of the cylinder 300 and the end wall 410 of the piston 400 are in contact with each other, a distal end of the piston 400 protrudes somewhat from the distal end of the cylinder 300. In other words, the length of the piston 400 along the longitudinal central axis $X_3$ is somewhat greater than the length of the circumferential wall 320 of the cylinder 300 along the longitudinal central axis $X_2$. Therefore, in the state shown in FIG. 2, a part of the rack 430 integrally formed on the outer peripheral surface of the piston 400 protrudes from the distal end of the cylinder 400. In this embodiment, the circumferential wall 320 of the cylinder 300 is formed with a linear notch 340 for exposing at least a part of the rack 430 of the piston 400. As explained in detail below, a sector gear 510 of the driving unit 500 meshes with the rack 430 through this notch 340 of the circumferential wall 320 of the cylinder 300.

As stated above, the system 10 comprises the driving unit 500 and the elastic member 600 mechanically associated with each other. The driving unit 500 can displace the piston 400 distally, i.e., in a direction in which a volume of the air intake space V in the cylinder 300 increases. On the other hand, the elastic member 600 is arranged to be deformed according to the displacement of the piston 400 and stores an elastic energy (mechanical potential energy) therein while the piston 400 is being displaced distally, i.e., in the direction in which the volume of the air intake space V increases. Therefore, the system 10 of this embodiment can be referred to as a "spring-loaded system". In this embodiment, as stated above, the elastic member 600 is a coil spring, which is housed inside the hollow piston 400 at least in part, for example, about half.

The driving unit 500 additionally comprises an elastic energy release mechanism M. In this embodiment the elastic energy release mechanism M is configured to release at a regular interval the elastic energy stored in the elastic member 600, thereby causing the piston 400 to rush (or dash) proximally, i.e., in a direction in which the volume of the air intake space V decreases. More specifically, the driving unit 500 comprises a sector gear 510 having teeth only in a certain angle range, such as, for example 90° to 300°. The sector gear 510 is arranged to mesh with the rack 430 of the piston 400 and drives it linearly in one direction (i.e., to the left side in the figure). In this embodiment, the combination of the sector gear 510 and the rack 430 forms the elastic energy release mechanism M for releasing a stored elastic energy at a regular interval. That is, at the moment when the last tooth of the sector gear 510 disengages from the last tooth of the rack 430, the restraint of the piston 400 is released, and thus the elastic energy stored in the elastic member 600 is also released instantly. However, in another embodiment, another type of the elastic energy release mechanism may be adapted and which may be configured to release the elastic energy stored in the elastic member 600 only when desired.

As already explained, the driving unit 500 comprises the electric power supply 520, for example, a rechargeable batteries such as lithium-ion batteries. Also, as explained above, the driving unit 500 comprises the electric motor 530 that is electrically connected to the electric power supply 520 and indirectly (that is, via a gear train for a power transmission) drives the sector gear 510 rotationally. The electric power supply 520, the electric motor 530, and the switch 580 interposed therebetween constitute the power source assembly **500*b* of the driving unit 500 as described above. In this embodiment, the sector gear 510 is rotated by the electric motor 530 via the group of gears 500*a* in only one direction, that is, counterclockwise in FIG. 2. In another embodiment, the sector gear 510 may be driven directly by the electric motor 530. However, in this case, since a motor having a large torque and therefore a large size is required, it is desirable to drive the sector gear 510** via a suitable reduction mechanism consisting of a gear train, as illustrated herein.

Here, referring to FIG. 4, the gear train constituting a reduction mechanism of the driving unit 500, i.e., the group of gears **500*a* of the driving unit 500 as stated above, will be described. The group of gears 500*a* of the driving unit 500 comprises a pinion 540 (of a bevel gear type) fixedly coupled to an output shaft 532 of the electric motor 530. Furthermore, the group of gears 500*a* of the driving unit 500 comprises two kinds of gears 550, 560 that transmit a rotational motion of the pinion 540 to the sector gear 510 to rotationally drive it. In this embodiment, these gears 550, 560 as well as the sector gear 510 are rotatably supported by the frame (not shown) of the system 10 (i.e., a subcase of the apparatus 1). Since the electric motor 530 is fixedly supported by the frame (not shown) of the system 10, the pinion 540 is also rotatably supported by the frame (not shown) of the system 10. In another embodiment, the gears 510, 550, and 560 may be rotatably supported by the casing 20 itself of the apparatus 1**.

Figure 4:
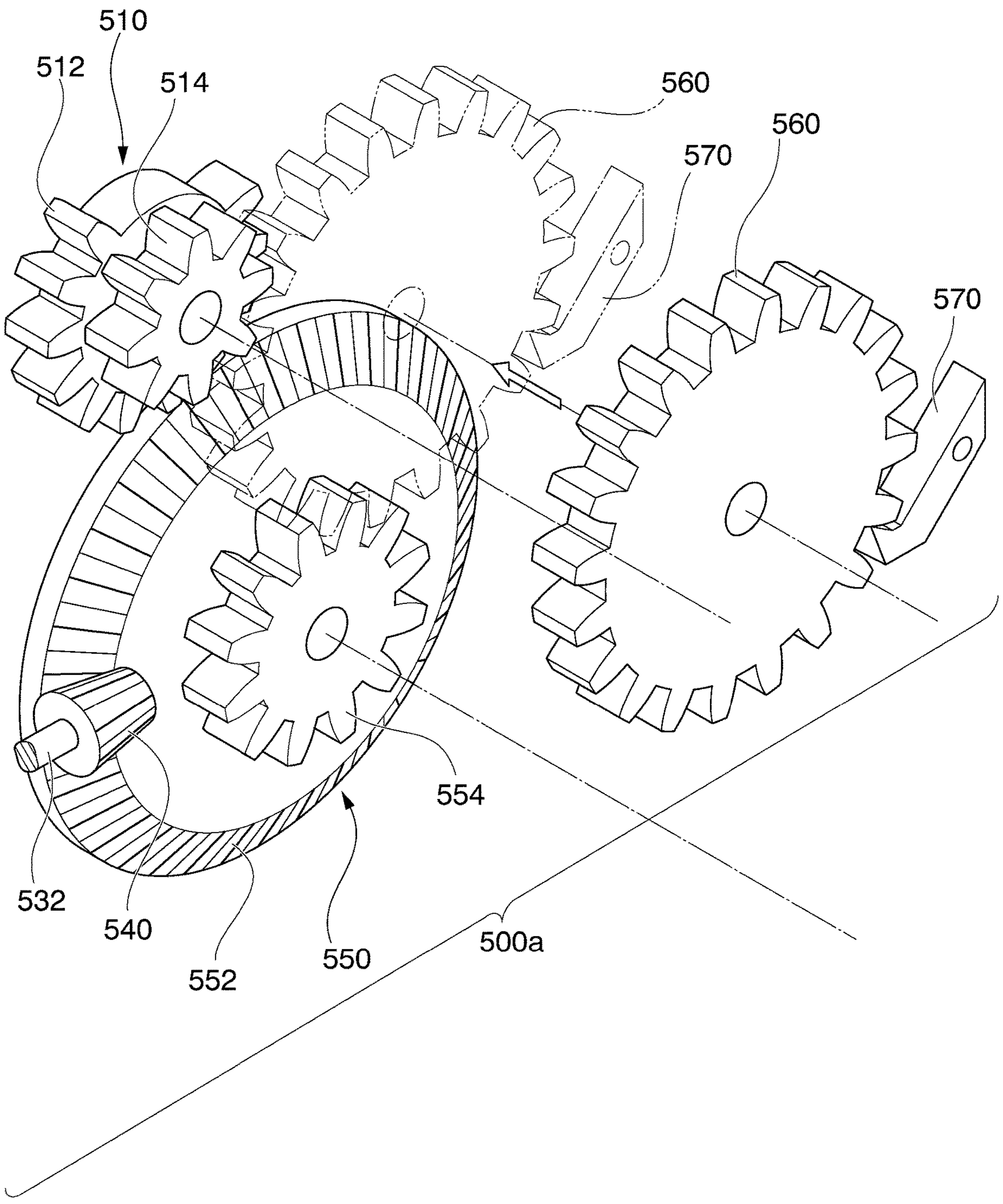
FIG. 4 is a perspective view showing various gears forming a driving force transmission mechanism of a driving unit of the system shown in FIG. 2, in a disassembled state.

Further referring to FIG. 4, the gear 550 that meshes with the pinion 540 is a bevel gear. On the other hand, the gear 560 that meshes with both the bevel gear 550 and the sector gear 510 is a spur gear. Here, the spur gear 560 functions as an intermediate gear. In this embodiment, both the sector gears 510 and the bevel gear 550 have a structure in which two types of gearing portions are stacked along the direction of rotational axis. The sector gear 510 comprises a first portion 512 with teeth only in a certain angular range along the root circle thereof. Furthermore, the sector gear 510 comprises a second portion 514 integrally coupled to this first portion 512. The second portion 514 of the sector gear 510, i.e., a spur gear portion, comprises teeth along the entire circumference of the root circle thereof. The diameter of the addendum circle of the second portion 514 is smaller than that of the first portion 512.

The bevel gear 550 also comprises a first portion 552 containing a row of teeth arranged circumferentially on a conical surface, and a second portion 554 integrally coupled to this first portion 552 and consisting of a spur gear smaller in diameter than the minimum diameter of the first portion 552. The pinion 540 fixedly attached to the output shaft 532 of the electric motor 530 meshes with the first portion 552 of the bevel gear 550, and the second portion 554 of the bevel gear 550 that rotates integrally with it meshes with the spur gear 560. Furthermore, the spur gear 560 meshes with a second portion 514 of the sector gear 510. As a result, the high speed rotation of the pinion 540 causes the sector gear 510 to rotate at a predetermined lower speed, for example, several revolutions per second. The piston 400 is displaced in the distal direction at a regular interval by the rotation of the sector gear 510 thus resulting. In this embodiment, the number of teeth on the rack 430 of the piston 400 is approximately equal to the number of teeth on the first portion 512 of the sector gear 510, but the present invention is not limited thereto.

Here, referring to FIG. 2 again, the driving unit 500 further comprises a latch 570 that meshes with the spur gear 560. The latch 570 is arranged so as to regulate a direction of rotation of the spur gear 560 so that the spur gear 560 rotates in only one direction (i.e., clockwise in FIG. 2). In another embodiment, it is also conceivable to engage the latch 570 with any other gear than the spur gear 560. The latch 570 is not a mandatory component in this system 10.

Further referring to FIG. 2, the system 10 additionally comprises an elongated spring guide rod 700, which is arranged so as to be surrounded by the coil spring 600. In this embodiment, a base end 710 of the guide rod 700 is supported by the frame (not shown) of the system 10 (i.e., a subcase of apparatus 1). In another embodiment, the spring guide rod 700 may be supported by the casing 20 itself of the apparatus 1. The spring guide rod 700 is arranged such that it at least partially enters the piston 400 when the piston 400 is being displaced distally, i.e., in the direction in which the volume of the air intake space V increases.

Hereinafter, the operation of the system 10 for atomizing and ejecting a liquid configured as described above, and therefore, a method for atomizing and ejecting a liquid for transdermal delivery will be described with reference to FIGS. 2, 5 to 8 (assuming that initially the tank 100 is empty).

Prior to an atomization and an ejection of a liquid, the tank 100 is filled with a liquid L. This process can be carried out with the tank 100 removed from the Venturi tube 200. Next, with the system 10, and therefore the apparatus 1 turned upside down, the tank 100 is screwed to the Venturi tube 200 to connect them with each other. The system 10 and therefore the apparatus 1 is then returned to the normal use position where the tank 100 is located above the Venturi tube 200. As a result of this process, the tank 100 is fluidly connected to the internal passage 210 of the Venturi tube 200 via the orifice 220 defined in the Venturi tube 200. This completes the preparation for atomizing and discharging the liquid (see FIG. 2). If a tank with an openable lid (in this case, the lid is provided opposite the flange 110 of the tank 100) is used, the tank 100 can be filled with liquid without removing it from the Venturi tube 200.

Figure 5:
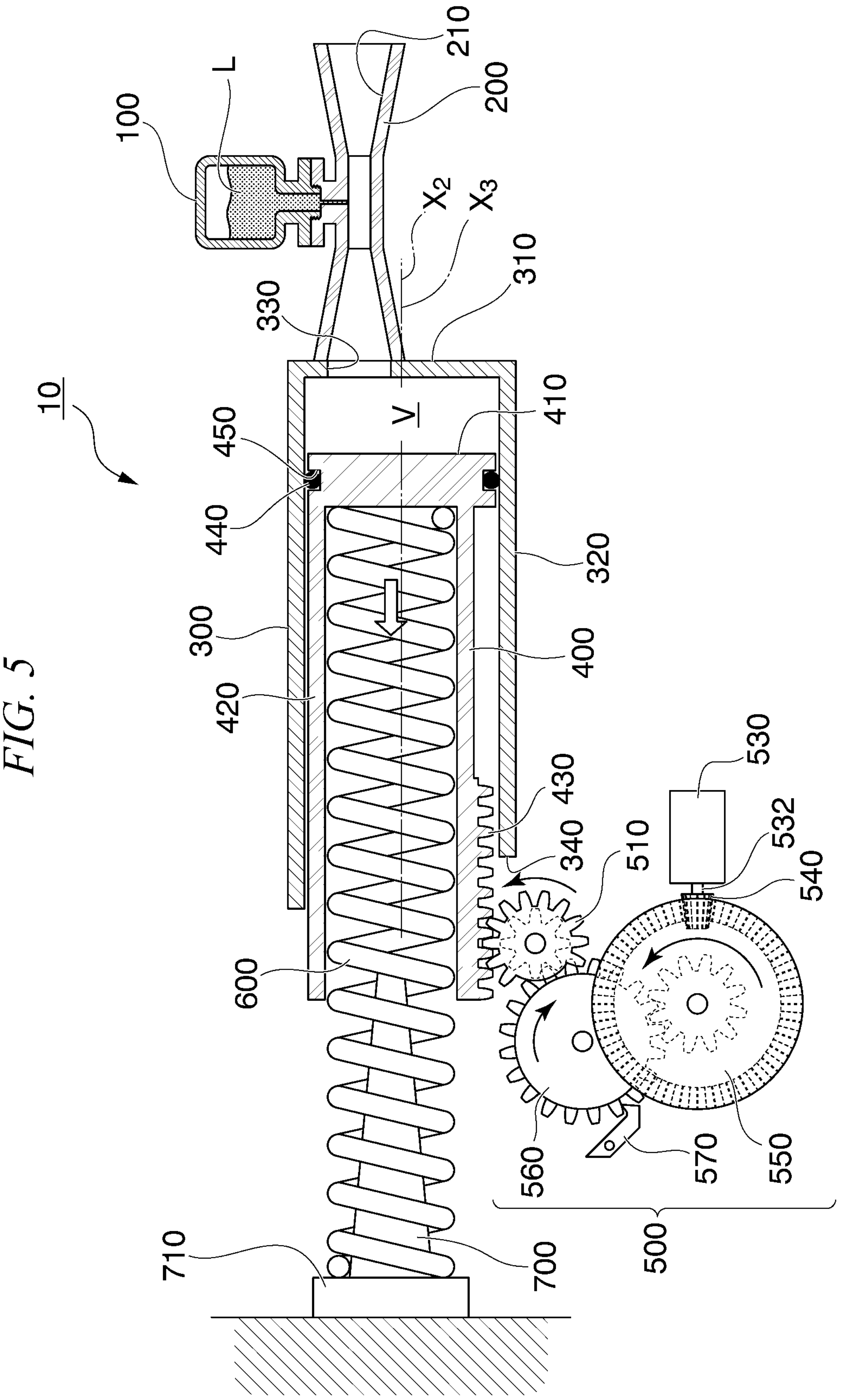
FIG. 5 is a schematic diagram similar to FIG. 2 of the system for atomizing and ejecting the liquid for a shallow transdermal delivery, showing a state in which the piston is being displaced distally (i.e., to the left side in the figure) by the driving unit.

Next, the piston 400 is displaced in the cylinder 300 distally, that is, in a direction in which a volume of an air intake space V defined in the cylinder 300 increases. This process is performed automatically by turning the switch 580 ON. That is, as described above, when the switch 580 is turned ON, the electric motor 530 rotates, and the rotational force thereof is transmitted to the sector gear 510 via the gear train consisting of the gears 550, 560. Since the sector gear 510 meshes with the rack 430 of the piston 400, the rotation of the sector gear 510 causes the piston 400 to be displaced distally as described above. FIG. 5 shows the state in which the piston 400 is being displaced only a short distance in the distal direction by the driving unit 500.

Figure 6:
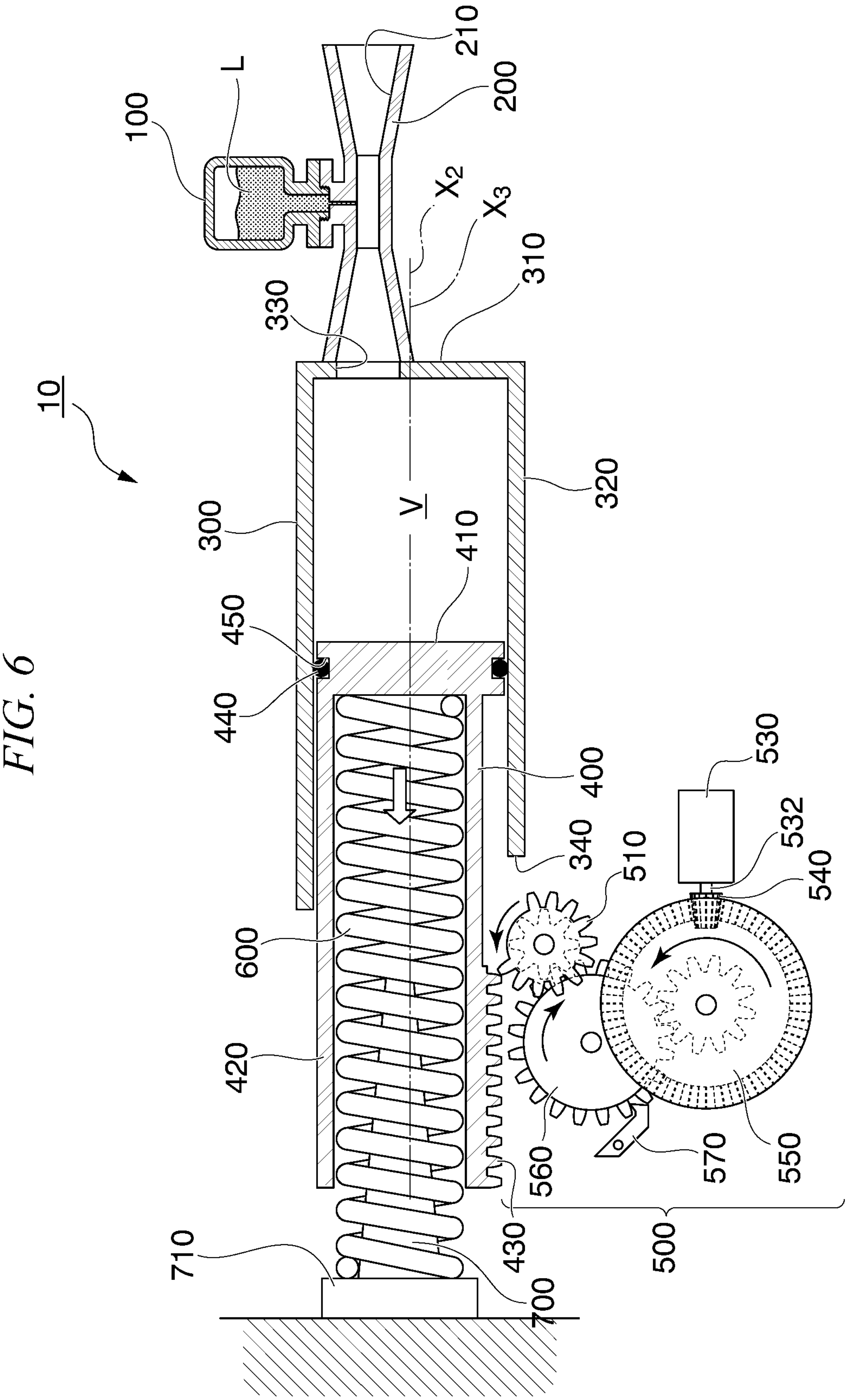
FIG. 6 is a schematic diagram similar to FIG. 2 of the system for atomizing and ejecting the liquid for a shallow transdermal delivery, where the piston has been displaced distally to its final position by the driving unit.

While the piston 400 is being displaced in the direction in which the volume of the air intake space V increases, the elastic member 600, i.e., the coil spring is simultaneously and gradually deformed. As stated above, the elastic member 600 is arranged so as to be deformed linearly according to the displacement of the piston 400. Therefore, during this process, the elastic member 600 stores an elastic energy therein. FIG. 6 shows the state in which the piston 400 has been displaced distally to its final position by the driving unit 500. This state is just before the last tooth (viewed in the direction of rotation) in the row of teeth of the sector gear 510 and the last tooth (viewed in the direction of displacement) of the rack 430 are disengaged, and the elastic energy stored in the coil spring 600 is maximized.

Figure 7:
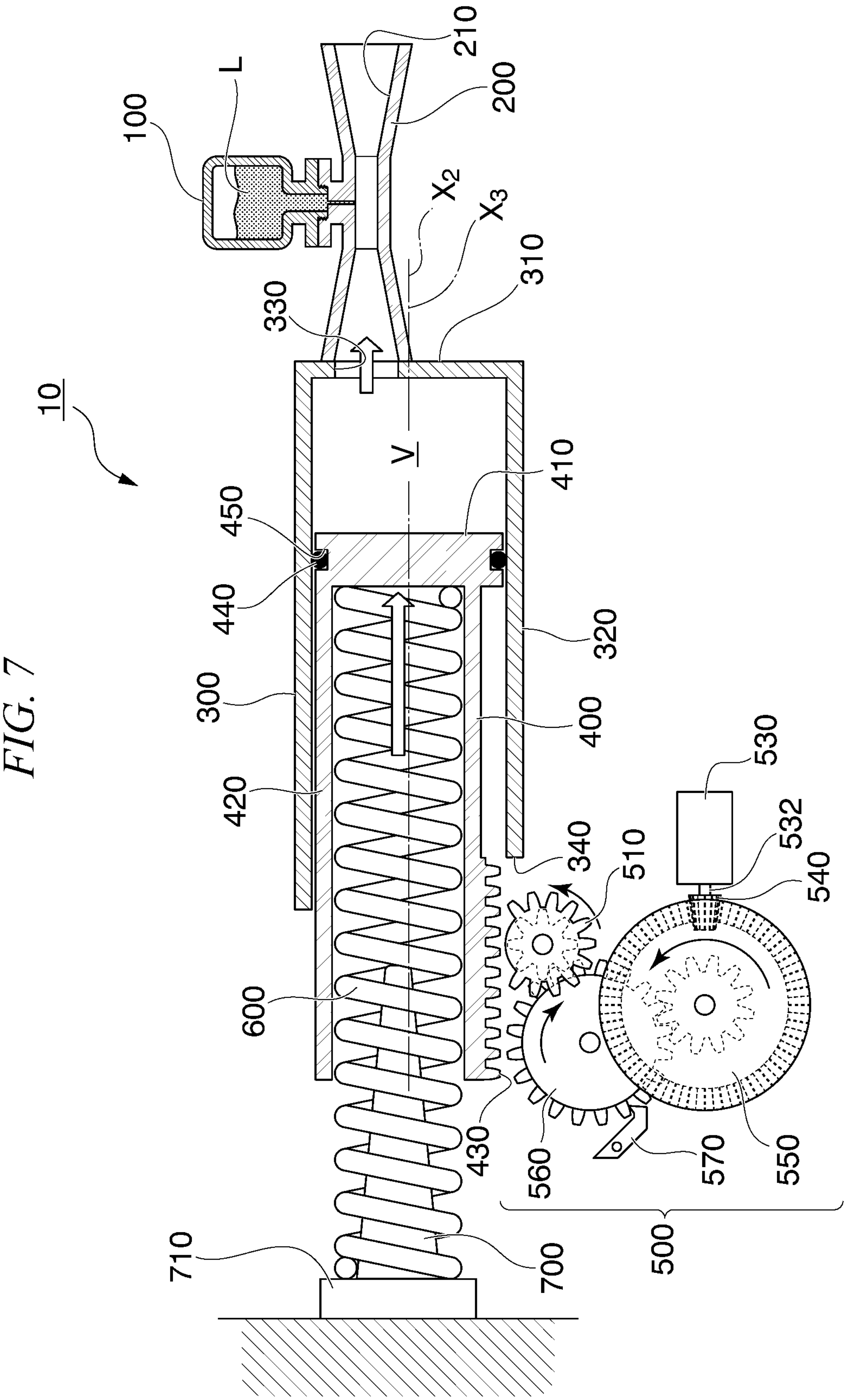
FIG. 7 is a schematic diagram similar to FIG. 2 of the system for atomizing and ejecting the liquid for a shallow transdermal delivery, where the elastic energy stored in a coil spring is released and the piston is being pushed back proximally (i.e., to the right side in the figure).

When the sector gear 510 is further rotated by a slight angle from the state shown in FIG. 6, the sector gear 510 and the rack 430, more specifically, the last tooth of the sector gear 510 and the last tooth of the rack 430 are disengaged. As a result, the piston 400 can now move freely. Therefore, the elastic energy stored in the elastic member 600 is instantly released, thereby causing the piston 400 to rush proximally, that is, in a direction in which the volume of the air intake space V decreases. FIG. 7 shows the state in which the piston 400 is pushed out proximally only a short distance in the cylinder 300.

Figure 8:
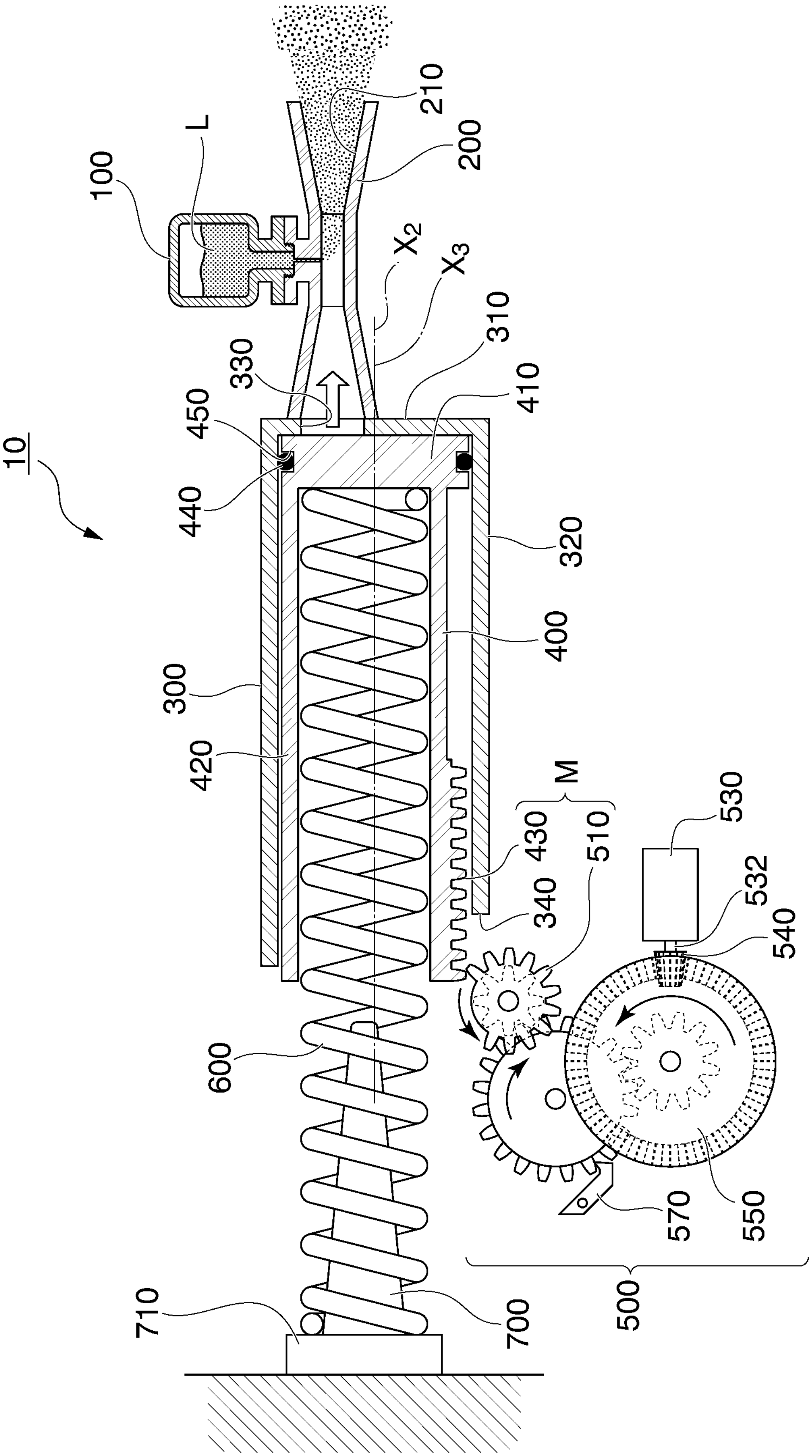
FIG. 8 is a schematic diagram similar to FIG. 2 of the system for atomizing and ejecting the liquid for a shallow transdermal delivery, where the piston collides with the end wall of the cylinder and a high-speed air pushed out of the cylinder causes the discharge of a mist of liquid from the outlet of the Venturi tube.

In the situation shown in FIG. 7, the air existing in the air intake space V in the cylinder 300 is compressed by the piston 400 and moves from the outlet hole 330 of the cylinder 300 into the Venturi tube 200 at a high speed. As air travels through the Venturi tube 200, the flow velocity of air increases, especially in its throat section 250. As a result, the pressure in the throat section 250 is reduced so that a small amount of liquid L in the tank 100 is drawn into the passage 210 through the orifice 220 of the Venturi tube 200. This small amount of liquid L is atomized inside the Venturi tube 200 by air that is pushed out of the cylinder 300 by a piston 400 and moves at high speed, and is discharged to the outside through the outlet 244 of the Venturi tube 200. FIG. 8 shows the state in which the piston 400 collides with the end wall 310 of the cylinder 300 and high-speed air pushed out of the cylinder 300 causes the discharge of a mist of liquid L from the outlet of the Venturi tube 200.

In this embodiment, unless the switch 580 is turned OFF, the electric motor 530 will continue to rotate, so the sector gear 510 will also continue to rotate. Therefore, immediately after reaching the state shown in FIG. 8, the sector gear 510 re-engages with the rack 430 of the piston 400. As a result, the system 10 returns to the initial state shown in FIG. 2. Accordingly, while the switch 580 keeps ON, the system intermittently atomizes the liquid L in the tank 100 (at an interval corresponding to the rotating speed of the sector gear 510) and discharges it as an atomized liquid particle through the Venturi tube 200 to the outside.

As stated above, the system 10, and thus apparatus 1 includes a compressed air source mainly consisting of the cylinder 300, the piston 400, the elastic member 600, and a driving unit 500, as well as the Venturi tube 200 in fluid communication with the fluid tank 100. The driving unit 500 displaces the piston 400 in the cylinder 300 with deformation of the elastic member 600, and thereby a predetermined amount of air is taken into the cylinder 300. Subsequently, by releasing the elastic energy stored in the elastic member 600, the piston 400 is pushed back to its original position in the cylinder 300 and compresses the air in the cylinder 300. As a result, the high-pressure air is blown out from the outlet hole 330 of the cylinder 300 at a high speed and supplied to the internal passage 210 of the Venturi tube 200. As the high-speed air passes through the Venturi tube 200, in particular, the throat section 250 (i.e., a constriction), the pressure inside it drops, so a small amount of liquid L in the tank 100 is taken into the internal passage 210 of the Venturi tube 200. A small amount of liquid L thus taken into is atomized inside the Venturi tube 200 by the action of the high-speed air and ejected out of the Venturi tube 200 together with the air. In this way, it is possible to provide a jet of finely atomized liquid, i.e., a high velocity atomized liquid particle (very fine size of droplet), suitable for a shallow transdermal delivery up to the upper epidermis layer of skin.

Furthermore, the system 10, and thus apparatus 1 do not require a replaceable, i.e., single-use/disposable motive power source such as a high-pressure gas cartridge in order to atomize and eject a liquid for a transdermal delivery. Therefore, the system 10, and thus the apparatus 1 can atomize and eject the liquid L over and over again. In addition to this, the system 10, and thus the apparatus 1 do not require an external source such as an air compressor or an air pump. That is, a high-speed air jet for atomizing and discharging a liquid are created internally. Therefore, the system 10, and thus the apparatus 1 can be compact as a whole and easy to move, transport and carry.

The specific data of one example of the system according to the above described embodiment are listed below. However, present invention is not limited by these values:

Inner diameter of the cylinder: 10 to 30 mm;

Spring constant of the elastic member: 20 to 70 N/m;

Natural length of the elastic member: 10 to 30 cm;

Outer diameter of the elastic member: 5 to 15 mm;

Diameter of the outlet hole of the cylinder: 1 to 10 mm, in particular, 5 mm;

Maximum inner diameter of the converging section of the Venturi tube: 1 to 10 mm, in particular 5 mm;

Maximum inner diameter of the diverging section of the Venturi tube: 7 mm when the maximum inner diameter of the converging section of the Venturi tube is 5 mm;

Inner diameter of the throat section of the Venturi tube: 3.4 mm when the maximum inner diameter of the converging section of the Venturi tube is 5 mm;

Inner diameter of the orifice of the Venturi tube: 0.6 to 1.2 mm, in particular, mm when the maximum inner diameter of the converging section of the Venturi tube is 5 mm;

Maximum pressure of the air compressed in the cylinder: 0.55 MPa;

Size of an atomized liquid droplet: under 10 μm;

Velocity of an atomized liquid droplet at the outlet of the Venturi tube: at least 150 m/s regardless of the molecular weight of the liquid;

Volume of the liquid that can be delivered: 20 ml/delivery (shot); and

Maximum frequency of the liquid delivery (shot): twice per second.

The preferred embodiments of the present invention have been explained above in detail referring to the drawings. However, the present invention is not limited to these embodiments, and various modifications and changes may be made to the above-described embodiments without deviating from the scope of the present invention, and such modifications and changes are also included in the scope of the present invention.

The invention claimed is:

1. A system for atomizing and ejecting a liquid and transdermally delivering the liquid, the system comprising:

a tank for holding the liquid;

a Venturi tube comprising: a first longitudinal central axis $X_1$; and an internal passage extending along the longitudinal central axis $X_1$, wherein the internal passage is connected to the tank via an orifice disposed in the Venturi tube, wherein the internal passage comprises: a converging section; a diverging section; and a throat section located between the converging section and the diverging section;

a cylinder comprising: a second longitudinal central axis $X_2$; a first end wall orthogonal to the second longitudinal central axis $X_2$; a circumferential wall extending from the first end wall along the second longitudinal central axis $X_2$; and an outlet hole formed on the first end wall, wherein the outlet hole is connected to an inlet of the converging section of the Venturi tube;

a piston arranged in the cylinder to be movable in the cylinder along the second longitudinal central axis $X_2$ thereof, wherein the piston forms an air intake space in the cylinder in cooperation with the cylinder, wherein the air intake space fluidly communicates with the inlet of the converging section of the Venturi tube via the outlet hole of the cylinder;

a driving unit configured to move the piston in a first direction to increase a volume of the air intake space in the cylinder; and an elastic member configured to deform based on the displacement of the piston and store an elastic energy generated while moving the piston in the direction to increase the volume of the air intake space, wherein the driving unit comprises an elastic energy release mechanism configured to release elastic energy stored in the elastic member to cause the piston to move in a second direction to decrease the volume of the air intake space, and wherein the piston comprises: a third longitudinal central axis $X_3$; a second end wall facing the first end wall of the cylinder; and a circumferential wall of the piston extending from the second end wall along the third longitudinal central axis $X_3$, wherein a rack extending along the third longitudinal central axis $X_3$ is formed on an outer surface of the circumferential wall of the piston, wherein the driving unit comprises a sector gear having teeth in a first angle range to allow the sector gear to mesh with the rack of the piston and drive the rack linearly, and wherein the elastic energy release mechanism comprises a combination of the sector gear and the rack.

2. The system of claim 1, wherein the driving unit further comprises: an electric power supply; and an electric motor electrically connected to the electric power supply, wherein the electric motor is configured to drive the sector gear rotationally.

3. The system of claim 1, wherein the driving unit further comprises: a pinion coupled to an output shaft of the electric motor; and one or more gears configured to transmit a rotational motion of the pinion to the sector gear to drive the sector gear rotationally.

4. The system of claim 1, wherein the one or more gears comprises: a bevel gear configured to mesh with the pinion; and a spur gear configured to mesh with both the bevel gear and the sector gear.

5. The system of claim 4, wherein the driving unit further comprises a latch configured to mesh with the spur gear to control the spur gear to rotate in a third direction.

6. The system of claim 1, wherein the circumferential wall of the cylinder comprises a linear notch for exposing at least a part of the rack of the piston, and wherein the sector gear is configured to mesh with the rack through the notch.

7. The system of claim 1, wherein the elastic member is a coil spring at least partially housed inside the piston.

8. The system of claim 1, further comprises an elongated guide rod surrounded by the elastic member, wherein the guide rod at least partially enters the piston when the piston moves in the first direction to increase the volume of the air intake space.

9. The system of claim 1, wherein the tank is connected to the throat section of the internal passage.

10. The system of claim 1, wherein the Venturi tube is directly connected to the cylinder to allow the inlet of the converging section of the Venturi tube and the outlet hole of the cylinder to be aligned with each other.

11. The system of claim 1, wherein a ratio of a maximum inner diameter $D_1$ of the converging section of the Venturi tube, an inner diameter $D_3$ of the throat section of the internal passage, and a maximum inner diameter $D_2$ of the diverging section of the internal passage is 1:(0.1 to 0.7):(1 to 1.5), based on the maximum inner diameter $D_1$ of the converging section.

12. The system of claim 1, wherein the liquid is a cosmetic liquid to be delivered transdermally.

13. An apparatus for transdermally delivering an atomized liquid, the apparatus comprising:

a system comprising:

a tank for holding the liquid;

a Venturi tube comprising: a first longitudinal central axis $X_1$; and an internal passage extending along the longitudinal central axis $X_1$, wherein the internal passage is connected to the tank via an orifice disposed in the Venturi tube, wherein the internal passage comprises: a converging section; a diverging section; and a throat section located between the converging section and the diverging section;

a cylinder comprising: a second longitudinal central axis $X_2$; a first end wall orthogonal to the second longitudinal central axis $X_2$; a circumferential wall extending from the first end wall along the second longitudinal central axis $X_2$; and an outlet hole formed on the first end wall, wherein the outlet hole is connected to an inlet of the converging section of the Venturi tube;

a piston arranged in the cylinder so as to be displaceable in the cylinder along the second longitudinal central axis $X_2$ thereof, wherein the piston forms an air intake space in the cylinder in cooperation with the cylinder, wherein the air intake space fluidly communicates with the inlet of the converging section of the Venturi tube via the outlet hole of the cylinder;

a driving unit configured to move the piston in a first direction to increase a volume of the air intake space in the cylinder; and an elastic member configured to deform based on the displacement of the piston and store an elastic energy generated while moving the piston in the first direction to increase the volume of the air intake space, wherein the driving unit comprises an elastic energy release mechanism configured to release elastic energy stored in the elastic member to cause the piston to move in a second direction to decrease the volume of the air intake space; and a casing configured to at least partially house the system, and wherein the piston comprises: a third longitudinal central axis X3; a second end wall facing the first end wall of the cylinder; and a circumferential wall of the piston extending from the second end wall along the third longitudinal central axis X3, wherein a rack extending along the third longitudinal central axis X3 is formed on an outer surface of the circumferential wall of the piston, wherein the driving unit comprises a sector gear having teeth in a first angle range to allow the sector gear to mesh with the rack of the piston and drive the rack linearly, wherein the elastic energy release mechanism comprises a combination of the sector gear and the rack.

14. The apparatus of claim 13, wherein the driving unit further comprises: an electric power supply; and an electric motor electrically connected to the electric power supply, wherein the electric motor is configured to drive the sector gear rotationally.

15. The apparatus of claim 14, wherein the driving unit further comprises: a pinion coupled to an output shaft of the electric motor; and one or more gears configured to transmit a rotational motion of the pinion to the sector gear to drive the sector gear rotationally.

16. The apparatus of claim 15, wherein the one or more gears comprises: a bevel gear configured to mesh with the pinion; and a spur gear configured to mesh with both the bevel gear and the sector gear.

17. The apparatus of claim 16, wherein the driving unit further comprises a latch configured to mesh with the spur gear to control the spur gear to rotate in a third direction.

18. A method for atomizing and ejecting a liquid and transdermally delivering the liquid, the method comprising:

filling a tank with the liquid, wherein the tank is connected to an internal passage of a Venturi tube via an orifice disposed in the Venturi tube, wherein the internal passage of the Venturi tube comprises: a converging section; a diverging section; and a throat section located between the converging section and the diverging section;

moving a piston in a cylinder in a first direction by a driving unit to increase a volume of an air intake space in the cylinder, wherein the air intake space is formed between the piston and a first end wall of the cylinder, wherein an outlet hole is formed on the first end wall of the cylinder and the outlet hole is connected to an inlet of the converging section;

moving the piston in the first direction to increase the volume of the air intake space and cause an elastic member to deform, wherein the elastic member is configured to deform according to a distance of the movement of the piston and store an elastic energy generated during the deformation;

releasing the elastic member to cause the piston to move in a second direction to decrease the volume of the air intake space; and atomizing and ejecting the liquid supplied from the tank into the internal passage, by moving the piston to push out air from the cylinder through the outlet hole of the first end wall of the cylinder, wherein the piston comprises: a third longitudinal central axis X3; a second end wall facing the first end wall of the cylinder; and a circumferential wall of the piston extending from the second end wall along the third longitudinal central axis X3, wherein a rack extending along the third longitudinal central axis X3 is formed on an outer surface of the circumferential wall of the piston, wherein the driving unit comprises a sector gear having teeth in a first angle range to allow the sector gear to mesh with the rack of the piston and drive the rack linearly, wherein the driving unit further comprises an elastic energy release mechanism configured to release elastic energy stored in the elastic member to cause the piston to move in a second direction to decrease the volume of the air intake space, wherein the elastic energy release mechanism comprises a combination of the sector gear and the rack.

* * * * *